United States Patent
Grainger et al.

(10) Patent No.: US 6,680,048 B2
(45) Date of Patent: Jan. 20, 2004

(54) ESTERS

(75) Inventors: Lynda Grainger, Wirral (GB); Kathryn Elizabeth Gransden, Wirral (GB); Andrew Hopkinson, Wirral (GB); Adam Jan Kowalski, Wirral (GB); Nicholas Webb, Wirral (GB); Michael Stephen White, Wirral (GB)

(73) Assignee: Unilever Home & Personal Care USA, a division of Conopco, Inc., Chicago, IL (US)

( * ) Notice: Subject to any disclaimer, the term of this patent is extended or adjusted under 35 U.S.C. 154(b) by 261 days.

(21) Appl. No.: 09/978,954

(22) Filed: Oct. 17, 2001

(65) Prior Publication Data

US 2002/0076385 A1 Jun. 20, 2002

(30) Foreign Application Priority Data

Oct. 17, 2000 (GB) .............................. 0025438

(51) Int. Cl.$^7$ .............................. A61K 7/32; A61K 7/34; A61K 7/36; C13K 13/00
(52) U.S. Cl. .......................... 424/65; 424/66; 424/400; 424/401; 536/123.13
(58) Field of Search .............................. 424/65, 66, 68, 424/400, 401; 536/123.13

(56) References Cited

U.S. PATENT DOCUMENTS

| | | | |
|---|---|---|---|
| 3,969,087 A | 7/1976 | Saito et al. | 44/7 |
| 4,673,570 A | 6/1987 | Soldati | 424/66 |
| 4,725,430 A | 2/1988 | Schamper et al. | 424/66 |
| 4,725,432 A | 2/1988 | May | 424/66 |
| 4,822,602 A | 4/1989 | Sabatelli | 424/65 |
| 4,948,578 A | 8/1990 | Burger et al. | 424/68 |
| 4,954,333 A | 9/1990 | Ward | 424/66 |
| 5,169,626 A | 12/1992 | Tanner et al. | 424/66 |
| 5,429,816 A | 7/1995 | Hofrichter et al. | 424/66 |
| 5,486,566 A | 1/1996 | Katsoulis | 524/773 |
| 5,587,153 A | 12/1996 | Angelone, Jr. et al. | 424/66 |
| 5,744,130 A | 4/1998 | Guskey et al. | 424/66 |
| 6,241,976 B1 * | 6/2001 | Esser et al. | 424/65 |

FOREIGN PATENT DOCUMENTS

| | | |
|---|---|---|
| EP | 512 770 | 10/1996 |
| WO | 92/19222 | 11/1992 |
| WO | 93/23008 | 11/1993 |
| WO | 97/11678 | 4/1997 |
| WO | 00/61079 | 10/2000 |
| WO | 00/61082 | 10/2000 |

OTHER PUBLICATIONS

Cosmetics and Toiletries, *Deodorant/Antiperspirant–Sticks*, 1990, vol. 105, p. 75–78.
GB Search Report in a GB Application, GB 0025437.5.
Bull. Chem. Soc. Japan (1195), 68(12), 3423–8. Abstract only.
Chem. Pharm. Bull. (1981), 29(2), 505–13. Abstract only.
Co–pending application: Applicant: Franklin et al., Ser. No. 09/982,150, Filed: Oct. 17, 2001.
Co–pending application: Applicant: Franklin et al., Ser. No. 09/982,077, Filed: Oct. 17, 2001.
European Search Report in an EP application 01 30 7826, 2002.
Takada et al., "Discotic Columnar Liquid Crystals In Oligosaccharide Derivatives III. Anomeric Effects On The Thermo–Mesomorphic Properties Of Cellobiose Octa–Alkanoates" Liquid Crystals, vol. 19, No. 4, pp. 441–448, 1995.

* cited by examiner

*Primary Examiner*—James O. Wilson
*Assistant Examiner*—Leigh C. Maier
(74) *Attorney, Agent, or Firm*—Kevin J. Stein

(57) ABSTRACT

Cellobiose esters and particularly α cellobiose octanonanoate has been found able to structure water-immiscible liquids well, and in particular can produce clear structured emulsions. However, such emulsions tend to lose clarity or structural strength during storage. Deviating from α-cellobiose octanonanoate can result in impaired clarity and/or impaired hardness of emulsion sticks. However, acylated cellobiose which contains acyl substituents of formula —O—CO—R in which R represents an n-octyl residue and the percentage Y of the nonanoate acyl substituent —O—CO—R at the anomeric carbon is at least 60% and the percentage A of α anomer is greater than the anomer and not higher than A=74.5 +0.2Y when Y is up to 92% and not higher than A=161–0.74Y when Y is greater than 92% offers the production of sticks combining structurant stability with product clarity and hardness.

31 Claims, No Drawings

ESTERS

The present invention relates to esters and in particular to esters of cellobiose, compositions containing them, and their use as structurants.

BACKGROUND

Many compositions intended for topical application to skin, including a number for various parts of the body, such as face, gums, hands, limbs, feet, torso, underarm, breasts, genitalia, hair and other parts of the body, comprise one or more active agents are distributed within or otherwise supported by a carrier fluid. Although it is possible, in many instances, that such compositions are in the form of lotions, it is often desirable that the active ingredient in such compositions, be it for medical or for cosmetic purposes, remains substantially localised in the region of the body to which it has been topically applied. In order to assist this to happen and also to enable alternative dispensers for the composition to be employed, the carrier fluid can be thickened or structured, for example by introducing one or more materials for that purpose. Thickened or structured compositions commonly adopt the form of firm sticks, or soft solids and creams. In such circumstances, the materials are often referred to as structurants or gelants and may sometimes alternatively as thickeners, depending on the final form of the composition. The carrier fluid may comprise water and/or a water-miscible organic liquid and alternatively or additionally a water-immiscible liquid.

In general, the choice of structurants or thickeners tends to vary in accordance with the physical nature of the carrier fluid and in particular on whether it is water-miscible or immiscible. The present invention is directed more particularly towards materials which are capable of structuring a water-immiscible liquid, which may act by itself as carrier for an active ingredient or comprise a water-immiscible phase in an emulsion or micro-emulsion or a liquid crystalline phase.

Many materials have been proposed for structuring or thickening a water-immiscible liquid phase of a composition intended for topical application to humans. These have included waxes natural waxes, such as paraffin waxes or those typically extracted from vegetation, such as candelilla wax, or glyceride waxes, or produced by chemical treatment of natural oils, for example hydrogenation of castor oil, or produced by extracted from fauna, such as beeswax or spermaceti wax, or derivatives or synthetic variants of them. Others include fatty alcohols, e.g. linear C18 or C22 alcohols. Other materials are polymeric, such as polysiloxane waxes, or polysiloxane elastomers, or various polyamide/polysiloxane copolymers.

In the closing years of the 20th century, a number of structurants were identified which the present inventors classify as fibre-forming. These include 12-hydroxy stearic acid, various amino acid amides, including particularly, combinations of sterols and sterol esters, for example, particularly, $\beta$-sitosterol and $\gamma$-oryzanol, derivatives of threitol, diamide derivatives of cyclohexane, and acylated derivatives of cellobiose. Each of the various structurants has to a greater or lesser extent its particular benefits and its intrinsic disadvantages, either in absolute or relative terms. These properties can include the ability of the material to gel or otherwise structure the carrier liquid, including the resultant hardness and stability, and the sensory properties and appearance of the resultant composition, being of great importance for cosmetic compositions.

One of the most desirable class of structurants comprises acylated cellobiose, as described in PCT application No PCT/GB 00/01228, published as WO 00/61079, particularly for structuring a water-immiscible liquid in a cosmetic compositions, including especially antiperspirant and deodorant compositions. In said PCT application, it has been disclosed that the cellobiose can adopt either an $\alpha$ or $\beta$ configuration, preferably the former, and various preferences are given for both the number of acyl substituents of the cellobiose nucleus and the chemical constitution of such substituents. Nonanoate esters of cellobiose (sometimes abbreviated to CB9) and particularly cellobiose octanonanoate in the predominantly $\alpha$ configuration is described therein as the most highly preferred acylated cellobiose, because CB9, particularly cellobiose octanonanoate, and specifically the $\alpha$ anomer is capable of structuring water-immiscible liquids that demonstrate an excellent combination of properties, namely high clarity and acceptable hardness when they are made.

However, it has been found that some samples of water-immiscible liquids which had been structured successfully using $\alpha$ anomeric CB9 tended to suffer from a loss of clarity after extended periods of storage and/or to exhibit some loss of structural strength. Either effect conveys self-evident disadvantages. Manifestly, if the stored product loses its structural strength, it can disintegrate under pressure. Alternatively an impairment in clarity is a visual cue which can be equated by consumers to impaired product performance. Formulations such as cosmetic formulations can take a long time to pass through conventional distribution channels or can sometimes remain unused for several months in consumers' homes.

Accordingly, it would be desirable to find a way to ameliorate or overcome the foregoing long-term disadvantages of $\alpha$ anomeric CB9 whilst at the same time retaining the capability of the material to act as a good structurant for water-immiscible liquids, and especially in the presence of a dispersed phase. It would be of only limited benefit if a solution that addressed the foregoing disadvantages on storage of CB9 structured formulations resulted in significant impairment of other and beneficial properties of the structured product.

It is an object of the present invention to provide an acylated cellobiose which demonstrates an attractive combination of properties in comparison with such $\alpha$ anomeric CB9, particularly in the context of acting as a structurant for a water-immiscible liquid.

Other and further objects of the present invention or aspects or embodiments thereof can be deduced from the disclosures hereinafter.

Research conducted by the instant inventors indicates that CB9 is a mixture of compounds which are present in varying proportions, depending on the method of manufacture and extent of blending. The overall properties of the mixture likewise vary. Three identifiable sub-classes of compounds have been found which contribute to the variation in properties. One sub-class comprises compounds in which the anomeric carbon is substituted by the nonanoate group in the axial orientation, called herein the $\alpha$ anomer, the second sub-class comprises compounds in which the anomeric carbon is substituted by the nonanoate group in the equitorial orientation, called herein the $\beta$ anomer, and the third sub-class comprises compounds in which the anomeric carbon is substituted by an hydroxyl group.

In particular, it has been found that the objects of the present invention can be achieved by suitable selection simultaneously of two parameters of CB9. One parameter comprises the proportion of the α anomer compared with the β anomer and the second parameter comprises the proportion of the hydrocarbon-containing substituent at the anomeric carbon in the acylated cellobiose structurant.

It will be understood, however, that although the material of the instant invention is contemplated especially for use in cosmetic formulations, its potential use is much wider, including the structuring of a water-immiscible liquid to make a cream, soft solid or stick for any other purpose. Such other purposes could include topical medicaments, topically applied veterinary products or animal cosmetics and waxes or polishes.

BRIEF DESCRIPTION OF THE INVENTION

According to a first aspect of the present invention, there is provided an acylated cellobiose which contains n-nonanoate acyl substituents of the cellobiose rings characterised in that the percentage Y of the nonanoate acyl substituent at the anomeric carbon in cellobiose is at least 60% and the percentage A of α anomer is greater than the β anomer and not higher than A=74.5+0.2Y when Y is up to 92% and not higher than A=161−0.74Y when Y is greater than 92%.

Without wishing the invention to be bound completely to a scientific theory or belief, it is believed that the absolute proportion of anomeric acylation and relative proportions of the two orientations of the nonanoate substituent at the anomeric carbon are both of great significance in identifying superior (and ideally optimal) CB9 material for structuring water-immiscible liquids.

By selecting the percentage Y of nonanoyl substituent —O—CO—R and the percentage A of α anomer in accordance with the first aspect of the present invention, it is possible to provide a structurant which can demonstrate an improved balance of properties compared with a similar structurant in which both Y and A are at 100% or close to 100%, and likewise with a similar structurant in which both Y and A are relatively low such as at or below 50%. In particular, by selecting the parameters A and Y within defined limits, it is possible to produce a structurant which can structure water-immiscible liquids having a suitable or preferred clarity and hardness on manufacture and which retain such desirable properties better during storage.

The present investigations have shown that the CB9 has a tendency to undergo crystallisation during storage, which is related to its Y and A proportions, and which is believed to have caused the change during storage in properties observed for products structured with approximately 100% α anomer and approximately 100% Y substitution. In particular, such a simultaneous selection of A and Y proportions according to the first aspect can show a suitable balance of stability to crystallisation, and hardness and/or clarity. Such materials demonstrate an excellent combination of properties suiting those materials particularly for structuring or thickening water-immiscible liquids, enabling them to be employed in the manufacture of base gels for cosmetic or medical actives.

The acylated cellobiose in accordance with the foregoing first aspect of the invention can be represented pictorially by general formula 1:

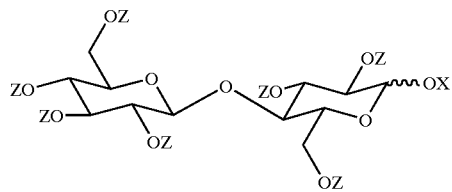

in which X and Z each represents either H or RCO— and R represents a saturated linear hydrocarbon residue of empirical formula —$C_8H_{17}$. X is a substituent at the anomeric position and Z is a substituent at the non-anomeric positions. Commonly, at least substantially all of the non-anomeric positions are acylated, and often all non-anomeric positions are acylated. Of the 8 available acylatable positions, greater than 7.5, on average are acylated.

In a second aspect of the present invention there is provided the use of an acylated cellobiose as described in the first aspect hereinabove for thickening or structuring a water-immiscible liquid, thereby forming a cream, soft solid or solid.

In a third aspect of the present invention, there is provided a base composition in the form of a cream, soft solid or solid containing a structurant or thickener an acylated cellobiose as described hereinabove in the first aspect In a related fourth aspect of the present invention, the base composition of the fourth aspect additionally contains an active cosmetic, medical, or veterinary agent.

DETAILED DESCRIPTION OF THE INVENTION AND PREFERRED EMBODIMENTS

Herein the acylated cellobiose compounds satisfy the Formula 1 shown above. The proportion (Y) of nonanoate acylation at the anomeric carbon by —O—CO—R is an important constituent of the first aspect of present invention. It is desirably at least 70% and preferably at least 80%. Herein a weight basis is employed when calculating percentages or proportions of acylation, as represented by peak areas in NMR determinations. The proportion can comprise up to 100% nonanoate acylation at the anomeric carbon. In many preferred embodiments, the proportion of nonanoate acylation (Y) at the anomeric carbon is greater than 85%, and in a number of convenient embodiments, it is at least 95%.

It will be understood that, when reference is made herein to nonanoate acylation, i.e. R in the acyl group R—CO—, it represents a saturated linear hydrocarbon residue of empirical formula —$C_8H_{17}$, in practice the acylating agent often comprises impurity proportions of one or more homologues or isomers, typically to not more than 5 molar %, including, in particular, ethanoate, n-octanoate, n-decanoate and isononanoate. Such homologues and isomers can accordingly constitute a fraction of the substituent at any position around the cellobiose and are contemplated within the instant invention.

The acylated cellobiose materials according to the present invention contain at least a preponderance of the α anomeric form in accordance with the limits specified hereinabove. It will be recognised that the remainder of the anomeric acylated cellobiose is present as the β anomer. Herein, since the α and β anomers have the same molecular weight, the proportion of α is same using either a molar and weight basis.

By application of the formulae for calculating the maximum proportion of the α anomer, it will be seen that the maximum proportion (A) of α anomer varies as the proportion of —O—CO—R substitution (Y) at the anomeric carbon varies. The maximum α anomer proportion peaks at 92.9% when the —O—CO—R substitution (Y) has a value of 92%, and declines when the —O—CO—R substitution (Y) is either higher or lower than 92%. Thus, A has a maximum value of 88.5% when Y=70%, a maximum value of 90.5% when Y=80, a maximum value of 91.5% when Y=85% and a maximum value of 92.9% when Y=92%. Similarly, A has a maximum value of 90.7% when Y=95, and a maximum value of 87% when Y=100%. Intermediate maximum values for A can be calculated. In some embodiments, it is advantageous for the acylated cellobiose to be chosen within 3% of the maximum value for A at the chosen value for Y. Preferably, the minimum value for A is at least 80% and in many instances is at least 82%. In a number of convenient embodiments, the A value is selected in the range of from 80% or 82% up to its calculated maximum and Y is at least 80% or at least 85%, e.g. from 85 to 95%.

It is especially desirable to select acylated cellobiose in which its A value is at least 80% and the Y value is at least 85% and in some embodiments is preferably at least 90%. In a number of practical and beneficial embodiments, the A value of the invention CB9 material is at least 82% and the Y value is at least 92%.

In certain especially desirable embodiments, the A value of the invention C9 material is equal to or greater than the value calculated by A%=157−0.74Y.

The selection of the A and Y values for the CB9 materials in accordance with the disclosure herein enables advantageous combinations of properties to be achieved, the precise selection depending on which property is accorded greater importance in the resultant structured liquid.

By the choice of acylated cellobiose with higher rather than lower A values, it is possible to obtain structured products which are harder rather than softer on manufacture, and by keeping the A value to at or below the maximum value identified above, it is possible to marry such beneficial hardness with inhibition or avoidance of crystallisation instability.

By the choice of a higher rather than a lower value for Y, it is possible to obtain structured products having a higher rather than a lower clarity on manufacture.

By selecting acylated cellobiose with higher values for Y in conjunction with a higher value for A, though not exceeding the maximum designated A value, it becomes possible to achieve a beneficial combination of clarity, and hardness coupled with stability against in situ crystallisation.

The invention CB9 compounds of the first aspect herein are at least substantially acylated at the non-anomeric position and at least partially acylated at the anomeric position. Normally, of the 8 acylatable positions in cellobiose, on average at least 7.5 of the positions are acylated. The extent and location of acylation, as well as orientation at the anomeric carbon, as would be expected, is dependent on the general method of preparation followed and the process conditions adopted in that method, such as reaction time, temperature and reagent and/or catalyst ratios.

Material Preparation

One way of making a product according to the first aspect of the present invention is to employ a modification to the process described in Example 1 of aforementioned PCT Application no PCT/GB 00/01228. In that Example, cellobiose was esterified with nonanoic acid to yield the fully esterified product in the form of its alpha-anomer, following a procedure generally as described in Takada et al, Liquid Crystals, Volume 19, page 441 (1995).

In the process employable herein, D-(+)-cellobiose is reacted with a molar excess of nonanoic acid, in the presence of a molar excess of trifluoroacetic anhydride (TFAA), in a mole ratio of 1:>15:>5. The reagents are charged into a reaction vessel that is equipped with heating, stirring and preferably liquid condensing means and heated with stirring and liquid reflux to an elevated temperature selected in the region of from 70 to 100° C. until a clear brown tinted mixture is obtained, such as an hour. The cellobiose is introduced gradually via a powder inlet and the reaction mixture is stirred at the elevated temperature for about 6 hours. The resultant mixture is cooled or allowed to cool to ambient temperature. CB9 crystals having A and Y values close to 100% precipitate out of solution when the mixture is introduced into a methanol:water mixture. The crystals can be purified by recrystallisation from a protic solvent system such as tetrahydrofuran/methanol.

By varying the reaction temperature whilst maintaining a specified mole ratio of acylating agent and catalyst to cellobiose, it is possible to vary the A value (i.e. proportion of alpha anomer) whilst keeping the Y value relatively unchanged. As the reaction temperature is increased, so the A value is increased. By varying the mole ratio of acylating agent and catalyst to cellobiose, whilst keeping the reaction temperature the same, it is possible to lower both the A and Y values, the Y value being lowered in the region of about twice as fast as the A value.

Accordingly, in order to obtain cellobiose esters having a high Y value such as in the region of 90% or higher and a desired A value, it is desirable to employ a relatively high ratio of acylating agent and catalyst to cellobiose, such as respectively a mole ratio of from 60 to 80:1 and 22 to 30:1 to cellobiose whilst select a suitable reaction temperature in the region of 70 to nearly 100° C. As the reaction temperature is increased from 70° C. to 95–100° C., the alpha value A increases from about 70% up to about 90% or higher. By selecting a lower mole ratio to cellobiose at 100° C. reaction temperature, the alpha and Y values are lower, so that at a mole ratio in the region of respectively 30 to 35:1 and 11 to 14:1 acylating agent and catalyst cellobiose, an acylated cellobiose is obtained having about 82% A and 66% Y values. Other combinations of A and Y values can be obtained by varying the reaction temperature within the specified range and choosing higher or lower reagent mole ratios in accordance with the principles outlined hereinabove.

A second method of obtaining CB9 materials having A and Y values within the ranges specified in the first aspect of the present invention comprises mixing two or more CB9 materials in a mathematically calculated weight ratio, one of which has an A and/or Y value above the desired value in the product mix, such as above the range specified in the first aspect and the second of which has an A and/or Y value below the desired value in the product mix, such as below the range specified in the first aspect. These mixtures may include at least one material having A and Y values within the range of the first aspect of the invention, and may be employed, for example, to fine tune the mixture.

Acylated cellobiose materials having both A and Y values at or close to 100% can be prepared by the method described hereinbefore, for example having A values above 92.5% by employing the aforementioned cellobiose: acylating agent and catalyst in a mole ratio of 1:>60:>22 at a reaction temperature of 100° C. Acylated cellobiose materials having A and Y values below 60% can be obtained by a similar acylation process, but using much lower molar excesses of acylating agent and catalyst, for example in the range of 1:<15:<5, and/or intermediate molar excesses 20–45:1 and 8 to 20:1 respectively at a reaction temperature in the lower end of the specified range, e.g. 70 to 80° C.

Further variations in the extent or pattern of acylation can be attained by variations in the acylating agent employed, in accordance with literature methods for acylating aliphatic or cycloaliphatic polyhydric substances.

A major intended use of the invention CB9 materials is as structurants for water-immiscible liquids, optionally in the presence of a dispersed solid or liquid phase. The amount of the invention CB9 structurant in a composition of this invention is likely to be from 0.1 or 0.5 to 20% by weight of the whole composition and preferably from 0.5 up to 15%, probably from 3 to 10% or from 10 to 13%. If the composition is an emulsion with a separate disperse liquid phase, the amount of invention CB9 structurant is likely to be from 0.5 to 25% or 30% by weight of the continuous water-immiscible phase, more likely from 5% to 20% or 25% of this phase.

Water-immiscible Liquid

The water-immiscible liquid, which in many embodiments acts as a carrier for a disperse solid or liquid phase, normally comprises one or a mixture of materials which are relatively hydrophobic so as to be immiscible in water. Some hydrophilic liquid may be included in the water-immiscible liquid, to the extent that it is soluble or miscible with the water-immiscible liquid and provided the overall carrier liquid mixture is still immiscible with water. It will generally be desired that this carrier is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable in some embodiments, that at least 80% by weight of the hydrophobic carrier liquid should consist of materials with a vapour pressure not over this value of 4 kPa at 25° C.

It is preferred, e.g. for use in cosmetic formulations that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), and the linear siloxanes normally exhibiting a viscosity of below $5\times10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic water-immiscible liquid carrier employed in many compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Selected polyalkylaryl siloxanes include short chain polysiloxanes, e.g. tri or tetrasiloxanes containing on average at least one phenyl group per siloxane unit, for example tetraphenyltrisiloxanes. Commercially available non-volatile silicone oils include Dow Corning 556 and Dow Corning 200 series. Other oils include Dow Corning 704.

The water-immiscible liquid carrier may contain from 0 to 100% by weight of one or more liquid silicones. Some embodiments herein contain silicone liquids in at least 10%, better at least 15%, by weight of the whole composition. If silicone oil is used, volatile silicone preferably constitutes from 10 to 100% of the weight of the carrier liquid. In many instances, when a non-volatile silicone oil is present, its weight ratio to volatile silicone oil is chosen in the range of from 1:3 to 1:40. In other embodiments, liquid silicones are absent or present in only a small proportion of the water-immiscible phase, such as up to 7 or 8%.

Silicon-free hydrophobic liquids can be used instead of, or in some embodiments in addition to liquid silicones. Silicon-free hydrophobic organic liquids which can be incorporated include volatile or non-volatile liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other hydrophobic carriers are liquid aliphatic or aromatic esters, but for some uses, for example antiperspirant formulations, these should be used as only part of the liquid carrier, desirably not above 20%, and possibly less than 10% by weight of the water-immiscible liquid carrier.

Suitable aliphatic esters contain at least one long chain alkyl group, such as esters derived from $C_1$ to $C_{20}$ alkanols esterified with a $C_8$ to C22 alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

Further instances of suitable hydrophobic carriers comprise liquid aliphatic ethers derived from at least one fatty alcohol, such as myristyl ether derivatives e.g. PPG-3 myristyl ether or lower alkyl ethers of polygylcols such as PPG-14 butyl ether.

Aliphatic alcohols which are solid at 20° C., such as stearyl alcohol are preferably absent or present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Silicon-free liquids can constitute from 0–100% of the water-immiscible liquid carrier. It is preferred that silicone oil and/or a hydrocarbon oil is present and that the total amount of other liquid carriers preferably constitute up to 50 or 60% for example from 0–10 or 10 to 40%% by weight of the water-immiscible carrier liquid.

An especially desired combination of water immiscible carrier liquids comprises a mixture of a silicone liquid such as a cyclomethicone and a hydrocarbon liquid, such as in a weight ratio of the former to the latter of from 3:2 to 1:10, optionally in the presence of an emollient water-immiscible liquid.

Emulsion

Many formulations according to the present invention also contain a more polar disperse phase. In such compositions, the invention CB9 material acts as a structurant in the continuous water-immiscible phase. The disperse phase may be a polar liquid alone or conveniently comprise a solution of an active ingredient, such as an antiperspirant salt.

The hydrophilic disperse phase in an emulsion normally comprises water as solvent and can comprise one or more water-soluble or water-miscible liquids in addition to or as a replacement for water. The proportion of hydrophilic carrier fluid, e.g. water, in the disperse phase, in an emulsion according to the present invention is often selected in the range of up to 60%, and particularly from 10% up to 40% or 50% of the whole formulation.

One class of water-soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

In an emulsion the disperse phase is likely to constitute from 5 to 80 or 85% of the weight of the composition preferably from 5 to 50 or 65% more preferably from 25 or 30% up to 50 or 65%, while the continuous phase with the structurant therein provides the balance from 15 or 35% up to 95% of the weight of the composition. Advantages can accrue when the internal phase volume constitutes a minor proportion of emulsion, such as from about 30 to 45% by weight. Yet other advantages arise at 45 to 65% internal phase volume. Compositions with high proportion of disperse phase, i.e. from-65 to 85% disperse phase, may also be advantageous. They can give good hardness even though the concentration of esterified saccharide structurant may be only a small percentage of the total composition.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 2 or 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10–25, steareth-10–25 (i.e. $C_{16}$ to $C_{18}$ alcohols ethoxylated with 10 to 25 ethylene oxide residues) and PEG-15–25 stearate or distearate. Other suitable examples include $C_{10}$–$C_{20}$ fatty acid mono, di or tri-glycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups. An especially desirable example of this class is available under the trade name ABIL EM90 for use within the aforementioned ranges of proportions.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPR™, Span™, Tween™, SF1228, DC3225C and Q2–5200.

Antiperspirant Actives

If the composition is an antiperspirant, it will contain an antiperspirant active. Antiperspirant actives, are preferably incorporated in an amount of from 0.5–60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration.

Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by wH2O. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_3CH(NH_2)CO_2H$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a composition normally includes the weight of any water of hydration and any complexing agent that may also be present in the solid active. However, when the active salt is in solution, its weight excludes any water present.

If the composition is in the form of an emulsion the antiperspirant active will be dissolved in the disperse phase. In this case, the antiperspirant active will often provide from 3 to 60% by weight of the aqueous disperse phase, particularly from 10% or 20% up to 55% or 60% of that phase.

Alternatively, the composition may take the form of a suspension in which antiperspirant active in particulate form is suspended in the water-immiscible liquid carrier. Such a composition will probably not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 μm with a mean particle size often from 3 to 20 μm. Both larger and smaller mean particle sizes can also be contemplated such as from 20 to 50 μm or 0.1 to 3 m.

Optional ingredients

Optional ingredients in compositions of this invention can include deodorants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as triclosan e.g. Igasan DP300™, Tricloban™, and Chlorhexidine warrant specific mention. A yet another class comprises biguanide salts such as those available under the trademark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Translucent/Transparent Compositions

When a composition of this invention is formulated as an emulsion it is possible to construct the formulation such that the emulsion is translucent or transparent. In order to do this the refractive indices of the water-immiscible continuous phase and the polar or aqueous disperse phase must be matched to each other and the value of refractive index at which they are matched must also approximately match the refractive index of the structurant.

The refractive index of a fibrous network of a structurant can be determined by using that structurant to gel a number of oils or oil mixtures of differing refractive index. The invention CB9 materials form fibrous networks having a refractive index which falls in a range between 1.45 and 1.50, being approximately 1.48 at 22° C.

For the continuous phase, silicon-free water-immiscible liquid oils generally have refractive indices in a range from 1.43 to 1.49 at 22° C. and can be used alone or mixed together to give a silicon-free carrier liquid with refractive index in this range. Volatile silicone oils generally have a refractive index slightly below 1.40 at 22° C., but carrier liquid mixtures with refractive indices in the range from 1.41 to 1.46 can be obtained by mixing volatile silicone with other oils. Non-volatile silicone oils generally have refractive indices in a range from 1.45 to 1.48 at 22° C. and so can be included when desired.

The RI of the continuous phase will be very close to the RI of the carrier liquid (usually a carrier liquid mixture) which is its principal component.

For the disperse phase, a solution of an antiperspirant active salt in water alone will generally display a refractive index below 1.425. The refractive index can be raised by incorporating a diol or polyol into the aqueous solution. It is believed to be novel to match the refractive index of a polar disperse phase to that of a structurant network within a continuous phase. Moreover, it can be achieved without using so much diol or polyol as will make the composition excessively sticky.

Mechanical Properties and Product Packages

The compositions of this invention are structured liquids and may be firm or soft in appearance. Even a soft solid has an ability to sustain its own shape, for instance if it is removed from a mould without being subjected to shear it will retain its shape for at least 30 seconds, usually longer.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a hand-wheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Having described the invention in general terms, specific embodiments are subsequently disclosed in greater detail hereinafter by way of example only.

EXAMPLE 1 AND COMPARISONS

In this Example and comparisons, a number of CB9 products were made having the proportions of α anomer (A) and nonanoyl substitution at the anomeric carbon (Y) specified in Table 2 below. Where indicated by Ex, the products are in accordance with the present invention and others indicated by C are included by way of comparison only.

The products were obtained by blending together one or more acylated cellobiose materials SM1 to SM9 having A and Y values as shown in Table 1 below. Materials SM1 to SM4, SM6, SM8 and SM9 were made by the following general method having mole ratios of reagents and catalyst as shown in Table 1.

General method for preparation of SM1 to SM4, SM6, SM8 and SM9. The general method is written at a scale of 20 g cellobiose and in some instances was scaled up between 15× to 20×.

Nonanoic Acid in an amount to provide the chosen mole ratio to the cellobiose was charged into a 2 liter flange pot equipped with an overhead stirrer, temperature probe, water condenser and addition inlet, together with the amount of trifluoroacetic anhydride needed to provide the chosen mole ratio to cellobiose. The resultant mixture was clear, and was then heated with stirring to an elevated reaction temperature of 70 to 100° C. using a silicone oil bath. During heating it was noted that the colour of the reaction mixture darkened and developed a dark brown tinge. After attaining 100° C., the stirred mixture was maintained at that temperature, first for one hour, and then whilst cellobiose (20 g, 0.058 moles) was slowly introduced over a few minutes via a solid powder addition funnel into the dark mixture. Immediately, a dirty brown suspension formed which then re-dissolved forming a clear black solution within 10–20 minutes. The reaction mixture continued to be stirred and maintained at 100° C. for a total of 6 hours and then cooled down to room temperature. The contents of the flask were transferred into 2 liters of methanol containing 10% de-ionised water in an ice-cooled 5 liter beaker. An off-white solid precipitated immediately of solution, which was filtered off and recrystallised a total of 4 times from a Tetrahydrofuran/Methanol solution producing a white solid product. The A and Y values of the product were then determined by the methods indicated below.

SM5 is obtainable by a route having mole ratio slightly above SM9 and SM7 is obtainable by a route having a mole ratio a little below SM8.

TABLE 1

|  | SM1 | SM2 | SM3 | SM4 | SM5 |
|---|---|---|---|---|---|
| mole ratio acylating agent: cellobiose | 64.5 | 32.2 | 32.2 | 64.1 | — |
| mole ratio TFAA: cellobiose | 25.5 | 12.2 | 12.2 | 24.3 | — |
| Reaction temp ° C. | 100 | 100 | 100 | 100 |  |
| % A | 93.5 | 81.5 | 83.4 | 100 | 84.9 |
| % Y | 98.0 | 55.6 | 62.0 | 99.5 | 98.2 |

|  | SM6 | SM7 | SM8 | SM9 |
|---|---|---|---|---|
| mole ratio acylating agent: cellobiose | 64.2 | — | 48.1 | 64.1 |
| mole ratio TFAA: cellobiose | 24.4 | — | 18.2 | 24.3 |
| Reaction temp ° C. | 100 | — | 100 | 75 |
| % A | 100 | 88.9 | 90.1 | 83.6 |
| % Y | 99.1 | 98.2 | 96.6 | 99.1 |

TABLE 2

| Ex or Comp | C1.1 | C1.2 | Ex1.3 | C1.4 | Ex1.5 |
|---|---|---|---|---|---|
| % Y | 99.5 | 98.0 | 98.2 | 89.2 | 88.5 |
| % A | 100 | 93.5 | 84.9 | 95.8 | 90.8 |
| % SM1 | 0 | 100 | 0 | 0 | 73.7 |
| % SM2 | 0 | 0 | 0 | 22.7 | 0 |
| % SM3 | 0 | 0 | 0 | 0 | 26.3 |
| % SM4 | 100 | 0 | 0 | 0 | 0 |
| % SM5 | 0 | 0 | 100 | 0 | 0 |
| % SN6 | 0 | 0 | 0 | 77.3 | 0 |

| Ex or Comp | C1.6 | Ex1.7 | C1.8 | C1.9 | C1.10 |
|---|---|---|---|---|---|
| % Y | 79.8 | 62.0 | 79.3 | 98.1 | 99.3 |
| % A | 91.3 | 83.4 | 91.6 | 95.1 | 91.8 |
| % SM2 | 0 | 0 | 45.5 | 0 | 0 |
| % SM3 | 52.6 | 100 | 0 | 0 | 0 |
| % SM4 | 47.4 | 0 | 0 | 50.0 | 50.0 |
| % SM6 | 0 | 0 | 54.5 | 0 | 0 |
| % SM8 | 0 | 0 | 0 | 50.0 | 0 |
| % SM9 | 0 | 0 | 0 | 0 | 50.0 |

| Ex or Comp | Ex1.11 | Ex1.12 | Ex1.13 | Ex1.14 | Ex1.15 |
|---|---|---|---|---|---|
| % Y | 88.5 | 78.7 | 79.5 | 88.7 | 98.2 |
| % A | 87.2 | 88.0 | 84.4 | 84.5 | 88.9 |
| % SM1 | 0 | 54.5 | 0 | 0 | 0 |
| % SM2 | 22.7 | 45.5 | 0 | 0 | 0 |
| % SM3 | 0 | 0 | 52.6 | 26.3 | 0 |
| % SM5 | 0 | 0 | 47.7 | 73.7 | 0 |
| % SM7 | 77.3 | 0 | 0 | 0 | 100 |

The %A (α anomer) and %Y (extent of acylation) at the anomeric carbon for all the source materials employed herein (SM1 to SM9 and SM10/SM11 or SM9/SM11 in respective subsequent Examples) were determined by $^1$H NMR spectroscopy, using a Bruker DRX 500 MHz NMR Spectrometer. The samples were run in 99.8 atom % D-Chloroform (CDC13) solvent containing 0.03% TetramethylSilane (TMS).

In the spectra obtained for acylated cellobiose using $^1$H NMR spectroscopy, the alpha and the beta anomeric forms have distinct peaks at distinct chemical shifts. The location of the peaks also depends on whether the anomeric carbon is substituted by hydroxyl or by an acyl group. These differences enable the user to distinguish between the alpha anomer, the beta anomer and the compounds that are hydroxyl-substituted at the anomeric carbon, and hence determine A and Y values.

A doublet at low field is due to the proton on the anomeric carbon of the alpha-anomer (J axial-equa=3.8 HZ; 6.26 ppm) when the anomeric carbon has been acylated, whereas the corresponding doublet is at a chemical shift of 5.36 ppm when its substituent is hydroxyl.

Correspondingly, the spectrum comprises a set of doublets at a higher field due to the proton at the anomeric carbon of the beta anomer (J axial-axial 7.9 HZ; 5.65 ppm) when the anomeric carbon is acylated and at a chemical shift of 4.82 ppm when the anomeric carbon is merely hydroxyl substituted. A linear comparison of the peak areas enables the relative proportions of the two anomers to each other (A value) and the acylated to hydroxyl-substituted compounds (Y value) to be determined.

The ability of $^1$H NMR spectroscopy to distinguish between acylated cellobiose molecules in which the cellobiose anomeric carbon is substituted by an hydroxyl or acyl group can be enhanced by employing a method in which the spectrum of the as-made sample is taken, the hydroxyl group in the sample is reacted with trichloroacetyl isocyanate (TCAI) and the spectrum of the sample is taken again. The chemical shift for TCAI-adducted alpha molecule is 6.33 ppm and for TCAI-adducted beta molecule is 5.73 ppm. By comparing the peak areas (PA) of the spectra, the relative proportions of the total hydroxyl ($PA_{TH}$), alpha acylated ($PA_\alpha$), and beta acylated molecules ($PA_\beta$) can be determined, and hence the Y and A values.

$$Y\% = 100(PA_\beta + PA_\beta)/(PA_\alpha + PA_\beta + PA_{TH})$$

$$A\% = 100\ PA_\alpha/(PA_\alpha + PA_\beta)$$

A second method employed to determine the proportion of CB9 acylated at its anomeric carbon and hydroxyl substituted anomeric carbon CB9 comprised reversed phase high pressure liquid chromatography (HPLC) with gradient elution and Evaporative Light Scattering Detection (ELSD). The apparatus used included a Hewlett Packard 1050 HPLC with an attached gradient pump and a $C_{18}$ end capped column (Hypersil ODS) Detection was carried out via a Polymer Lab ELS 1000 Mass Detector.

All solvents used were of HPLC grade.

20 μl of a solution of 0.025 g of sample dissolved in 1.0 ml chloroform was injected and eluted using the following chromatographic conditions:

Mobile Phase=Gradient

| Time (mins) | THF (%) | Methanol (%) |
|---|---|---|
| 0 | 7 | 93 |
| 25 | 80 | 20 |

Flow Rate/Flux (mls/min)=1.2, Gas Flow=50 mls Nitrogen/min

The results are given in area percent.

EXAMPLE 2

In this Example (including internal comparisons), clear emulsion sticks were made using the products of Example 1 to structure the water-immiscible phase of a formulation having the general composition summarised in Table 3 below by the general method outlined below.

TABLE 3

| Ingredients | % w/w |
|---|---|
| Cyclomethicone DC245 (1) | 17.6 |
| Polydecene (2) | 26.4 |
| Acylated Cellobiose –C9 of Ex 1 | 5.0 |
| Cetyl Dimethicone Copolyol (3) | 1.0 |
| Zirconal 50 (4) | 40.0 |
| Glycerol (5) | 10.0 |

Legend
(1) DC245 (Dow Corning)
(2) Hydrogenated Polydecene, Silkflo 364NF (Albemarle)
(3) Abil EM90 (Th. Goldschmidt) [emulsifier]
(4) 50% aqueous solution of Al/Zr pentachlorohydrate (Giulini)
(5) Glycerol (Aldrich)

Stick Manufacture General Method

The oils (1 and 2) and surfactant (3) were mixed together and heated to 5–10° C. above the predetermined dissolution temperature of C9 acylated cellobiose blend, with gentle stirring in a Silverson mixer. Thereafter the acylated cellobiose CB9 blend was introduced and the conditions maintained until it had all dissolved. The aqueous phase comprising the Zirconal solution and glycerol was heated to the same temperature as the oil phase, and then added slowly over 1 minute into the oil phase, the shear rate having been increased to 7500 rpm. Once addition was complete, the formulation was held at the same temperature, first for 5 minutes whilst it was stirred at 7500 rpm and thereafter for a further minute with gentle stirring before being poured into clear glass-walled 15 cm³ jars and allowed to cool to room temperature.

Test Method

The glass jars containing the formulations were stored at 25° C. in a storage cabinet and examined at regular intervals to determine whether there was any discernible difference to the stick, and particular in regard to the crystallisation of the structurant CB9. The glass jars were inspected by carefully removing them individually from the storage cabinet, holding them vertically, shining a beam of light horizontally onto their side wall and observing whether they were any crystals visible to the naked eye of an experienced observer. The results after 6 months storage are summarised in Table 3 below, a ✓ indicating that crystallisation was observed and a × indicating that it was not.

TABLE 4

| Ex / Comp | C1.1 | C2.2 | Ex2.3 | C2.4 | Ex2.5 |
|---|---|---|---|---|---|
| CB9 from | C1.1 | C1.2 | Ex1.3 | C1.4 | Ex1.5 |
|  | ✓ | ✓ | X | ✓ | X |
| Ex / Comp | C2.6 | Ex2.7 | C2.8 | C2.9 | C2.10 |
| CB9 from | C1.6 | Ex1.7 | C1.8 | C1.9 | C1.10 |
|  | ✓ | X | ✓ | ✓ | ✓ |
| Ex / Comp | Ex2.11 | Ex2.12 | Ex2.13 | Ex2.14 | Ex2.15 |
| CB9 from | Ex1.11 | Ex1.12 | Ex1.13 | Ex1.14 | Ex1.15 |
| Stability | X | X | X | X | ✓ |

From Table 3, it can be seen that formulations structured with CB9 materials according to the present invention were stable in the test against crystallisation, whereas those structured with the same amount of materials not according to the present invention were not stable to crystallisation.

EXAMPLE 3

This Example demonstrates that the clarity of structured water-immiscible liquid at the time of preparation diminishes as the proportion Y diminishes. A gel was obtained by heating the selected blend of fluids according to the legend in Example 2 to a temperature of approximately 100° C., adding 10% w/w of the structurant with gentle stirring into the hot fluid, and maintaining the conditions until the structurant had dissolved completely, and thereafter pouring the product into a cell and permitting the material to cool to ambient (about 25° C.).

The CB9 material was obtained by blending SM10, a sample of CB9 having Y=100% (and A=approx. 100%), with SM11, a sample of CB9 in which Y=0. SM10 sample was made by a process as described in Example 1 employing a mole ratio of acylating agent and TFAA catalyst to cellobiose of respectively about 65:1 and 25:1 at a reaction temperature of 100° C. SM11 sample with Y=0 was obtained by partially deacylating, i.e. at the anomeric carbon, a sample having A and Y values of approximately 100% and made by the same process as SM10. In SM11, since Y=0, it contains no anomeric nonanoate substitution, and thus A=0.

The deacylation step was carried out as follows. Glacial acetic acid (2.04 g) was added slowly drop-wise with stirring into a solution of ethylenediamine (4.09 g) in tetrahydrofuran (THF, 850 cm³). A white precipitate formed which remained during the reaction. α-Cellobiose octanonanoate (50 g) was then added and the whole reaction mixture stirred at room temperature for a total of 48 hours.

At the end of the reaction period, the contents of the flask were transferred to a two liter separating funnel, 350 cm³ of water was added and the mixture extracted with dichloromethane (250 cm³). The organic layer was collected and further washed with successive 350 cm³ portions of (1) dilute HCl (0.1M), (2) aqueous sodium bicarbonate (1M) and (3) water.

The resultant organic phase was recovered, dried over anhydrous magnesium sulphate, filtered and the remaining solvent removed by a rotary evaporation. An off-white crude solid was obtained which was recrystallised from THF/methanol (50:300 cm³). A white solid precipitated out on overnight storage.

The proportion of light transmitted through the structured fluid was measured using the method indicated below. The results are summarised in Table 5 below.

TABLE 5

|  | Weight ratio of SM10:SM11 | 80% of (2): 20% of (1) % T |
|---|---|---|
| Ex3.1 | 70% SM10 30% SM11 | 12.67 |
| Ex3.2 | 60% SM10 40% SM11 | 3.445 |
| Ex3.3 | 50% SM10 50% SM11 | 0.85 |

Table 5 shows that the proportion of light transmitted increases sharply as the Y value for the CB9 is increased through 60%, i.e. as the proportion of SM10 in the mixture increases and likewise, as the A value increases.

Measurement of Light Transmission

The translucency of a composition was measured by placing a sample of standardised thickness in the light path of a spectrophotometer and measuring transmittance, as a percentage of light transmitted in the absence of the gel.

This test was carried out using a dual-beam spectrophotometer. The sample of composition was poured hot into a 4.5 ml cuvette made of polymethylmethacrylate (PMMA) and allowed to cool to an ambient temperature of 20–25° C. Such a cuvette gives a 1 cm thickness of composition. Measurement was carried out at 580 nm, with an identical but empty cuvette in the reference beam of the spectrophotometer, after the sample in the cuvette had been held for 24 hours.

EXAMPLE 4

This Example further demonstrates that clarity in structured sticks increases as the value of Y increases. The light transmission of the sticks produced in Comparison C6 and in Ex5 was measured by the method described in Example 3 above. Both CB9 structurants had similar A values of respectively 91.3 and 90.8%, but Y values of respectively 79.8 and 88.5%. The light transmission was 18.7% in C6 but increased to 38% in Ex5.

The clarity of the sticks produced in Examples Ex3 and Ex14 were similarly measured. The structurant in both sticks had a similar A value, respectively 84.9 and 84.5%, but Y values that differed markedly, namely 98.2 in Ex3 and 88.7% in Ex14. The respective light transmissions were 65.3% and 44.8%.

The results in this Example show that it is desirable to employ CB9 having a higher Y value, preferably at least 85% and more preferably at least 90% and, in the light of Example 2, whilst selecting A and Y values such that the structurant is resistant to crystallisation during storage.

EXAMPLE 5

In this Example, the procedure of Example 3 was followed, but employing blends of SM9 and SM11 as identified hereinbefore in Examples 1 and 3 respectively to gel a solvent mixture of hydrogenated polydecene and volatile silicone fluid, (2) and (1) respectively in the legend of Example 2, at a 10% by weight concentration.

TABLE 6

| | Weight ratio of SM9:SM11 | A% value/Y% value | 60%:40% (2):(1) % T |
|---|---|---|---|
| Ex5.1 | 90% SM9 10% SM11 | 83.6/89.6 | 32.3 |
| Ex5.2 | 80% SM9 20% SM11 | 83.6/79.3 | 18.9 |

Table 6 demonstrates not only that it is possible to obtain a gel having significant light transmittance when Y is close to 80% and A is above 80%, but also that an improvement in clarity is obtained when Y is increased to approximately 90% at the same A value.

EXAMPLE 6

This Example demonstrated the change in hardness of sticks structured with CB9 structurants having differing A values.

The hardness was measured by ball indentation (texture analyser) employing the method described below.

The hardness of the sticks produced in Ex 2.5 and Ex 2.14 was respectively 0.101 and 0.056 N/mm$^2$. The structurants had a similar Y value (88.5 and 88.7%) but differing A values of respectively 90.8 and 84.5%.

Similarly the hardness of the sticks produced in C2 and Ex 3 was respectively 0.107 and 0.066 N/mm$^2$. The structurants had a similar Y value (98.0 and 98.2%) but differing A values of respectively 93.5 and 84.9%.

From the results in Example 6, it can be seen that to make sticks, it would be desirable to employ CB9 structurants having a high A value, because such sticks have a higher hardness, but it will also be seen by a comparison with the data in Example 2 that this desideratum is in conflict with the desire for the structurant to be resistant to crystallisation. Thus, this Example together with Example 2 shows that it is desirable to employ a CB9 structurant having a higher rather than a lower A value, but to the extent that the structurant is stable, ie within the range defined by the upper limit for A.

Measurement of Hardness by Texture Analyser

In this test apparatus, a blunt probe is moved into or out from a sample at a controlled speed and at the same time the applied force is measured. The parameter which is determined as hardness is a function of the peak force and the projected area of indentation.

A specific test protocol used a Stable Micro systems TA.XT2i Texture Analyser. A metal sphere, of diameter 9.5 mm, was attached to the underside of the Texture Analyser's 5 kg load cell such that it could be used for indenting a sample placed beneath it on the base plate of the instrument. After positioning the sample, the sphere position was adjusted until it was just above the sample surface. Texture Expert Exceed software was used to generate the subsequent motion profile used in the test method. This profile initially indented the sphere into the sample at an indentation speed of 0.05 mm/s until a designated force was reached, which was chosen such that the distance of penetration into the sample was less than the radius of the sphere. At this load the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

The samples in the 15 ml jars needed no surface preparation but each had enough surface area for only a single indentation test to be performed.

The data associated with each test were manipulated using standard spreadsheet software and used to calculate the hardness, H, using the following equation: where $F_{max}$ is the peak load and $A_p$ is the projected area of the indentation remaining on unloading. This area can be calculated geometrically from the plastic indentation depth. This is slightly less than the total penetration depth measured under load because of elastic deformation of the sample. The plastic indentation depth is calculated from a graph of the unloading-force-versus-total-penetration-depth. The initial slope of this unloading data depends on the initial elastic recovery of the sample. The plastic indentation depth is estimated from an intercept between the zero force axis and a straight line drawn at a tangent to the initial part of the unloading slope.

Similar hardness measurements were also done using a desktop Instron Universal Testing Machine (Model 5566) fitted with a 10 N load cell, and the data analysis performed in the same way.

We claim:

1. An acylated cellobiose which contains nonanoate acyl substituents wherein the percentage Y of the nonanoate acyl substituent at the anomeric carbon of the cellobiose is at least 60% and the percentage A of α anomer is greater than the β anomer and not higher than A=74.5+0.2Y when Y is up to 92% and not higher than A=161−0.74Y when Y is greater than 92%.

2. An acylated cellobiose according to claim 1 wherein the percentage A of α anomer is equal to or greater than A=157−0.74Y when Y is greater than 92%.

3. An acylated cellobiose according to claim 1 wherein the percentage Y of the nonanoate substituent at the anomeric carbon is at least 70%.

4. An acylated cellobiose according to claim 1 wherein the percentage Y of the nonanoate substituent at the anomeric carbon is at least 80%.

5. An acylated cellobiose according to claim 1 wherein the percentage Y of the nonanoate substituent at the anomeric carbon is at least 85%.

6. An acylated cellobiose according to claim 5 wherein the percentage Y of the nonanoate substituent at the anomeric carbon is at least 95%.

7. An acylated cellobiose according to claim 1 wherein the percentage A of α anomer is at least 70%.

8. An acylated cellobiose according to claim 1 wherein the percentage A of α anomer is at least 80%.

9. An acylated cellobiose according to claim 8 wherein the percentage A of α anomer is at least 82%.

10. An acylated cellobiose according to claim 1 wherein the percentage Y of the nonanoate substituent at the anomeric carbon is at least 80% and the percentage A of α anomer is at least 80%.

11. A method of thickening or structuring a water-immiscible liquid to form a cream, soft solid or solid comprising the steps forming a solution of a gelant comprising an acylated cellobiose of claim 1 in the water-immiscible liquid at a temperature above its gelling temperature and thereafter cooling the solution to and maintaining it at below its gelling temperature until its viscosity has increased or it has solidified.

12. A method of thickening or structuring a water-immiscible liquid according to claim 11 wherein the percentage Y of the nonanoate substituent at the anomeric carbon in the acylated cellobiose is at least 80% and the percentage A of α anomer is at least 80%.

13. A cream, soft solid or solid base composition comprising water-immiscible liquid structured or thickened by an effective amount of an acylated cellobiose as specified in claim 1.

14. A cream, soft solid or solid base composition according to claim 13 wherein the percentage Y of the nonanoate substituent at the anomeric carbon in the acylated cellobiose is at least 80% and the percentage A of a anomer is at least 80%.

15. A composition according to claim 13 which contains the acylated cellobiose in an amount selected in the range of from 0.1 to 20% by weight thereof.

16. A composition according to claim 13 which contains the acylated cellobiose in an amount selected in the range of from 0.5 to 15% by weight thereof.

17. A composition according to claim 13 which is in the form of an emulsion, and in which the amount of the acylated cellobiose is from 5 to 30% by weight of its combined weight with the water-immiscible liquid.

18. A composition according to claim 13 which additionally contains one or more active agents selected from skin benefit agents, personal care agents, medicaments, sunscreen or tanning aid.

19. A composition according to claim 18 in which the active agent is dissolved or suspended in the water-immiscible liquid.

20. A composition according to claim 19 in which the personal care agent comprises an antiperspirant or deodorant active.

21. A composition according to claim 13 in which the water-immiscible liquid comprises a silicone oil, a liquid hydrocarbon or a mixture thereof.

22. A composition according to claim 13 in which the thickened or structured water-immiscible liquid forms an emulsion or micro-emulsion or a liquid crystalline phase with an aqueous or water-miscible liquid.

23. A composition according to claim 22 which additionally contains one or more active agents selected from skin benefit agents, personal care agents, medicaments, sunscreen or tanning aid.

24. A composition according to claim 23 in which the one or more active agent is dissolved in the aqueous or water-miscible liquid.

25. A composition according to claim 22 in which the emulsion is a water-in-oil emulsion.

26. A composition according to claim 25 in which the oil comprises a water-immiscible liquid selected from the group consisting of a silicone oil, a liquid hydrocarbon or a mixture thereof.

27. A composition according to claim 25 in which the personal care agent comprises an antiperspirant or deodorant active.

28. A composition according to claim 27 in which the active is an aluminium salt, or a salt containing aluminium and zirconium.

29. A composition according to claim 28 in which the active is aluminium chlorohydrate, aluminium and zirconium chlorohydrate or a complex of aluminium and zirconium chlorohydrate with glycine.

30. A cosmetic method for preventing or controlling perspiration which comprises applying topically to skin a composition according to claim 13 additionally containing an antiperspirant active.

31. A cosmetic method for treating skin which comprises applying topically to skin a composition according to claim 13 additionally containing a cosmetic active.

\* \* \* \* \*